(12) United States Patent
Zhang et al.

(10) Patent No.: US 11,747,008 B2
(45) Date of Patent: Sep. 5, 2023

(54) DEEP ULTRAVIOLET LIGHT SOURCE

(71) Applicant: BOLB INC., San Jose, CA (US)

(72) Inventors: Jianping Zhang, San Jose, CA (US); Ling Zhou, San Jose, CA (US); Ying Gao, San Jose, CA (US); Huazhong Deng, San Jose, CA (US); Alex Lunev, San Jose, CA (US); Cuong Le, San Jose, CA (US)

(73) Assignee: BOLB INC., Livermore, CA (US)

( * ) Notice: Subject to any disclaimer, the term of this patent is extended or adjusted under 35 U.S.C. 154(b) by 91 days.

(21) Appl. No.: 17/197,721

(22) Filed: Mar. 10, 2021

(65) Prior Publication Data

US 2022/0290851 A1    Sep. 15, 2022

(51) Int. Cl.
| | | |
|---|---|---|
| F21V 29/60 | (2015.01) | |
| F21V 7/04 | (2006.01) | |
| F21V 29/51 | (2015.01) | |
| F21V 29/76 | (2015.01) | |
| H01L 33/48 | (2010.01) | |
| H01L 33/62 | (2010.01) | |
| H01L 33/58 | (2010.01) | |
| H01L 25/075 | (2006.01) | |
| F21Y 105/10 | (2016.01) | |
| F21Y 115/10 | (2016.01) | |

(52) U.S. Cl.
CPC ............. *F21V 29/60* (2015.01); *F21V 7/041* (2013.01); *F21V 29/51* (2015.01); *F21V 29/767* (2015.01); *H01L 25/0753* (2013.01); *H01L 33/486* (2013.01); *H01L 33/58* (2013.01); *H01L 33/62* (2013.01); *F21Y 2105/10* (2016.08); *F21Y 2115/10* (2016.08)

(58) Field of Classification Search
CPC .................... F21Y 2105/10; F21Y 2115/10
See application file for complete search history.

(56) References Cited

U.S. PATENT DOCUMENTS

| | | | | |
|---|---|---|---|---|
| 2008/0149962 A1* | 6/2008 | Kim | ........................ | H01L 23/62 |
| | | | | 257/E33.001 |
| 2014/0084317 A1* | 3/2014 | Lee | .......................... | H01L 33/58 |
| | | | | 257/98 |
| 2014/0209928 A1* | 7/2014 | Teng | ..................... | H01L 25/167 |
| | | | | 257/82 |

* cited by examiner

*Primary Examiner* — Andrew J Coughlin
(74) *Attorney, Agent, or Firm* — J.C. PATENTS

(57) ABSTRACT

A DUV light source module includes a print circuit board, an array of DUV light-emitting diodes (LEDs), a plurality of DUV LED drivers for driving the DUV light-emitting diodes, and a pair of electrical connectors for connecting the DUV LED drivers hence the DUV light-emitting diodes to a power source, and A DUV light source device includes the DUV light source module, a reflector, a heat sink, a heat pipe, a radiator and a fan.

18 Claims, 16 Drawing Sheets

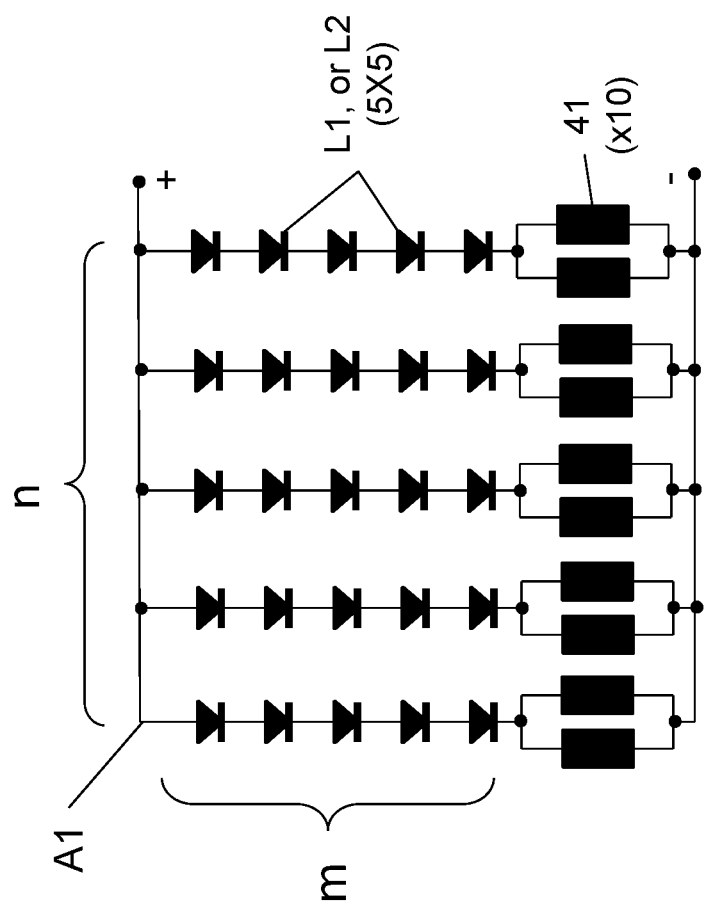

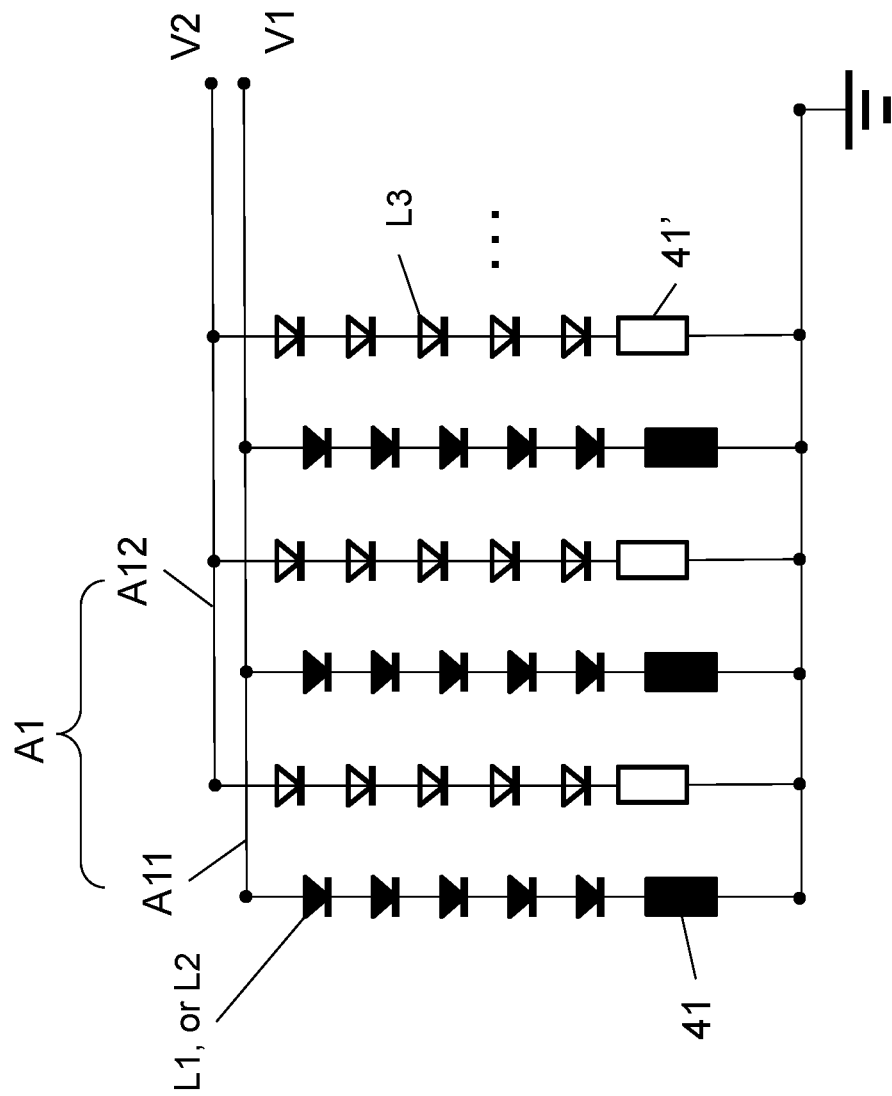

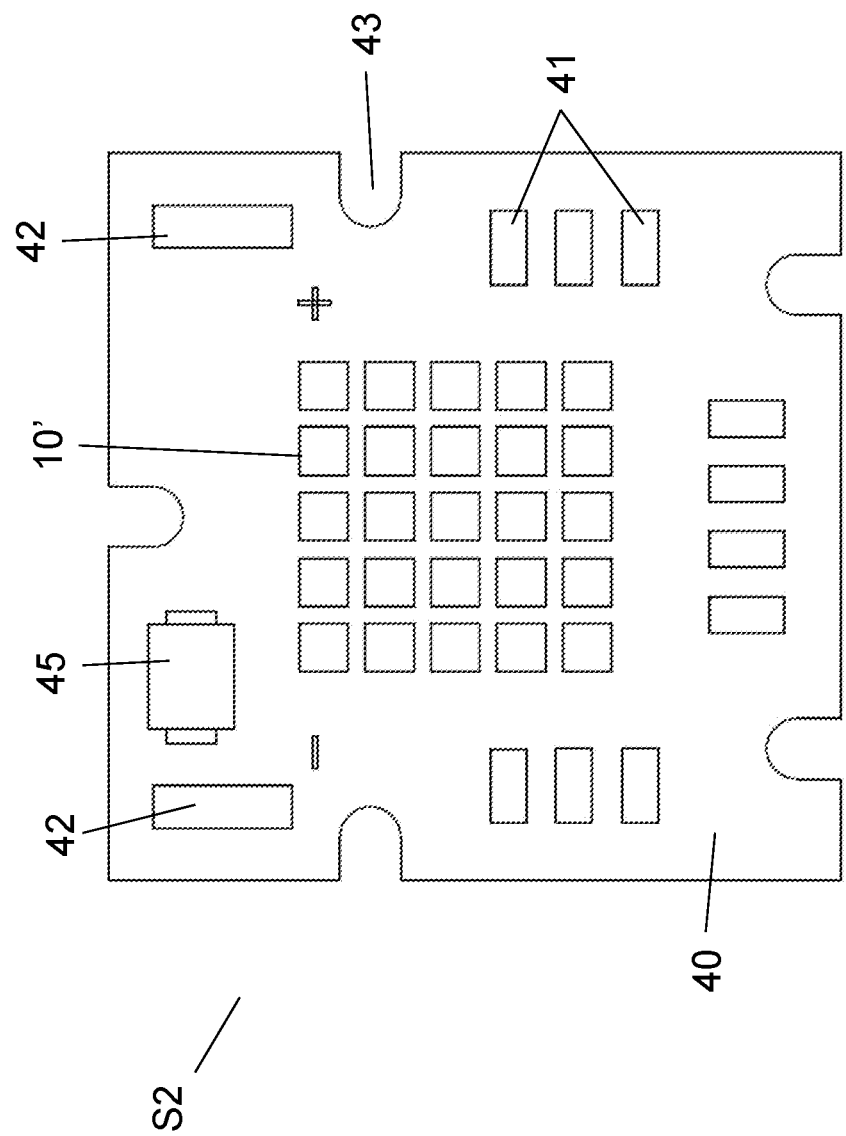

DEEP ULTRAVIOLET LIGHT SOURCE

FIELD OF THE INVENTION

The present disclosure relates to a deep ultraviolet light source and, more particularly, to an instant-on high-intensity deep ultraviolet light source for germicidal and virucidal applications.

DESCRIPTION OF THE RELATED ART

Evidences reveal that surface and airborne viruses are responsible for epidemic outbreaks. Deep ultraviolet (DUV) light in the UV-C region, i.e., light with wavelengths from 200 to 280 nm, has been proven to be germicidal and virucidal efficient for long. A recent research paper from Columbia University revealed that a DUV dose as low as 1.7 $mJ/cm^2$ achieved a 99.9% deactivation rate of airborne Human Coronavirus (HCov-229E), a safe subrogate for severe acute respiratory syndrome coronavirus 2 (SARS-CoV-2) that causes Covid-19 disease (see: M. Buonanno, D. Welch, I. Shuryak, and D. Brenner, Scientific Reports, 10 (10285), 2020). A direct disinfection test of SARS-COV-2 viruses showed that a 3 $mJ/cm^2$ GUV dose resulted in 99.7% Covid-19 virus deactivation rate (see: H. Kitagawa, T, Nomura, T. Nazmul, K. Omori, N. Shigemoto, T. Sakaguchi, and H. Ohge, American J. Infection Control, 000 (2020), 1-3). DUV light sources, however, have to possess further features such as instant-on, high-intensity, safety, and commercial viability before general adoption for mitigation of pandemic/epidemic events.

In the past, DUV light generated by mercury and xenon lamps has been used in hospitals for disinfection. The problems with these gas source DUV lamps include not only safety concerns as toxic chemicals and fragile quartz sleeves being involved but also the lack of immediate response on demand as the lamp gases need warm-up time to get into excited states to emit light. For example, mercury lamps may need a warm-up time (to warm the mercury vapor) from 2 to 30 minutes before reaching their full output powers. Further, as gas source DUV lamps utilizing low-pressure gas plasma as lighting media, the light intensity is weak and sensitive to ambient temperature. An intensity deviation up to a few hundred percent can occur when ambient temperature changes from 40 to 0° C.

To address the above and other problems in this filed, the present disclosure provides an instant-on high-intensity DUV light source made of nitride compound semiconductor light-emitting diodes (LEDs). Nitride compound semiconductor such as InN, GaN, AlN, and their ternary and quaternary alloys enable UV emissions ranging from 410 nm approximately to 200 nm, including UV-C (280-200 nm) emissions. DUV light sources according to the present disclosure possess instant-on and high-intensity features with transient time constant in the microseconds and less, and with intensity on the optical axis decaying approximately inversely proportional to the square of the distance to the light source, yet maintaining intensity larger than 2 $W/m^2$ (0.2 $mW/cm^2$) on the optical axis at one meter away from the light source.

SUMMARY OF THE INVENTION

A first aspect of the disclosure provides a DUV light source module, which includes a print circuit board, an array of DUV light-emitting diodes (LEDs), a plurality of DUV LED drivers for driving the DUV light-emitting diodes, and a pair of electrical connectors for connecting the DUV LED drivers hence the DUV light-emitting diodes to a power source, wherein the array of DUV light-emitting diodes comprises an integrated silicon (Si) submount and a plurality of DUV LED chips, the integrated silicon submount is electrical insulating and contains an array of cavities with slanted reflective sidewall; each of the DUV LED chips is disposed in a corresponding cavity of the array of cavities, respectively; and the integrated silicon submount is bonded on the print circuit board.

A second aspect of the disclosure provides a DUV light source module, which includes a print circuit board, an array of DUV light-emitting diodes (LEDs), a plurality of DUV LED drivers for driving the DUV light-emitting diodes, and a pair of electrical connectors for connecting the DUV LED drivers hence the DUV light-emitting diodes to a power source, wherein the array of DUV light-emitting diodes comprises multiple DUV LEDs individually bonded on the print circuit board, each of the DUV LEDs comprises a DUV LED chip, a surface mount, and a lens covering the DUV LED chip, the surface mount includes an electrically insulating body and four bond pads, two of the four bond pads are bonded to an n-bond pad and a p-bond pad of the DUV LED chip, respectively, and the other two of the four bond pads are bonded to their respective n- and p-bond pads on the print circuit board;

wherein an area of the p-bond pad on the DUV LED chip is at least 60% of an area of the DUV LED chip, and an area of the n-bond pad is about 10%-15% of the area of the DUV LED chip;

wherein the lens is a single lens having a partial sphere shape or a hemisphere shape, or the lens is a nested lens which includes a spheric or hemispheric lens, an inter-lens cavity, and a tall lens taller than the spheric or hemispheric lens, the inter-lens cavity physically separates the spheric or hemispheric lens and the tall lens, being DUV light transparent and having a refractive index lower than that of the spheric or hemispheric lens and the tall lens.

A third aspect of the disclosure provides a DUV light source module, which includes a print circuit board, an array of DUV light-emitting diodes (LEDs), a plurality of DUV LED drivers for driving the DUV light-emitting diodes, and a pair of electrical connectors for connecting the DUV LED drivers hence the DUV light-emitting diodes to a power source, wherein the DUV light-emitting diodes are connected in an m×n matrix, including n branches of LEDs connected in parallel, each branch of LEDs contains m DUV LEDs connected in series and has its own DUV LED driver, wherein each of the DUV light-emitting diodes comprises a DUV LED chip and a lens covering the DUV LED chip, and the DUV LED chip is directly boned on the print circuit board with an n-bond pad and a p-bond pad of the DUV LED chip bonded to their corresponding n- and p-bond pads on the print circuit board, respectively, wherein the lens is a single lens having a partial sphere shape or a hemisphere shape, or the lens is a nested lens which includes a spheric or hemispheric lens, an inter-lens cavity, and a tall lens taller than the spheric or hemispheric lens, the inter-lens cavity physically separates the spheric or hemispheric lens and the tall lens, being DUV light transparent and having a refractive index lower than that of the spheric or hemispheric lens and the tall lens.

A fourth aspect of the disclosure provides a DUV light source device, which includes a DUV light source module according to the first aspect, a reflector, a heat sink, a heat pipe, a radiator and a fan, wherein the DUV light source module is fastened to the heat sink, a part of the heat pipe is attached to the heat sink, and the radiator is fastened to and in contact with another part of the heat pipe, the fan blow air through the radiator; during operation, heat generated by the DUV light source module is transferred to the heat sink and then conducted to the part of the heat pipe attached to the heat sink, making a phase-changing media within the part of the heat pipe vaporize and carrier heat to the another part of the heat pipe which is fastened to the radiator and cooled by the fan.

A fifth aspect of the disclosure provides a DUV light source device, which includes a DUV light source module according to the second aspect, a reflector, a heat sink, a heat pipe, a radiator and a fan, wherein the DUV light source module is fastened to the heat sink, a part of the heat pipe is attached to the heat sink, and the radiator is fastened to and in contact with another part of the heat pipe, the fan blow air through the radiator; during operation, heat generated by the DUV light source module is transferred to the heat sink and then conducted to the part of the heat pipe attached to the heat sink, making a phase-changing media within the heat pipe vaporize and carrier heat to the another part of the heat pipe which is fastened to the radiator and cooled by the fan.

A sixth aspect of the disclosure provides a DUV light source device, which includes a DUV light source module according to the third aspect, a reflector, a heat sink, a heat pipe, a radiator and a fan, wherein the DUV light source module is fastened to the heat sink, a part of the heat pipe is attached to the heat sink, and the radiator is fastened to and in contact with another part of the heat pipe, the fan blow air through the radiator; during operation, heat generated by the DUV light source module is transferred to the heat sink and then conducted to the part of the heat pipe attached to the heat sink, making a phase-changing media within the heat pipe vaporize and carrier heat to the another part of the heat pipe which is fastened to the radiator and cooled by the fan.

BRIEF DESCRIPTION OF THE DRAWINGS

The accompanying drawings, which are included to provide a further understanding of the invention and constitute a part of this application, illustrate embodiments of the invention and together with the description serve to explain the principle of the invention. Like reference numbers in the figures refer to like elements throughout, and a layer can refer to a group of layers associated with the same function.

FIG. 2B presents a schematic electrical circuit diagram of a deep UV light source module according to an embodiment of this disclosure.

FIG. 2C presents a schematic electrical circuit diagram of a deep UV light source module according to an embodiment of this disclosure.

FIG. 5 shows a schematic plan view of a deep UV light source module according to an embodiment of this disclosure.

DETAILED DESCRIPTION OF EMBODIMENTS

In the following description, for the purposes of explanation, specific details are set forth in order to provide an understanding of the disclosure. It will be apparent, however, to one skilled in the art that the disclosure can be practiced without these details. One skilled in the art will recognize that embodiments of the present disclosure, described below, may be performed in a variety of ways and using a variety of means. Those skilled in the art will also recognize that additional modifications, applications, and embodiments can be made based on this disclosure and are within the scope thereof, as are additional fields in which the disclosure may provide utility. Accordingly, the embodiments described below are illustrative of specific embodiments of the disclosure and are meant to avoid obscuring the disclosure.

Figure 1A:
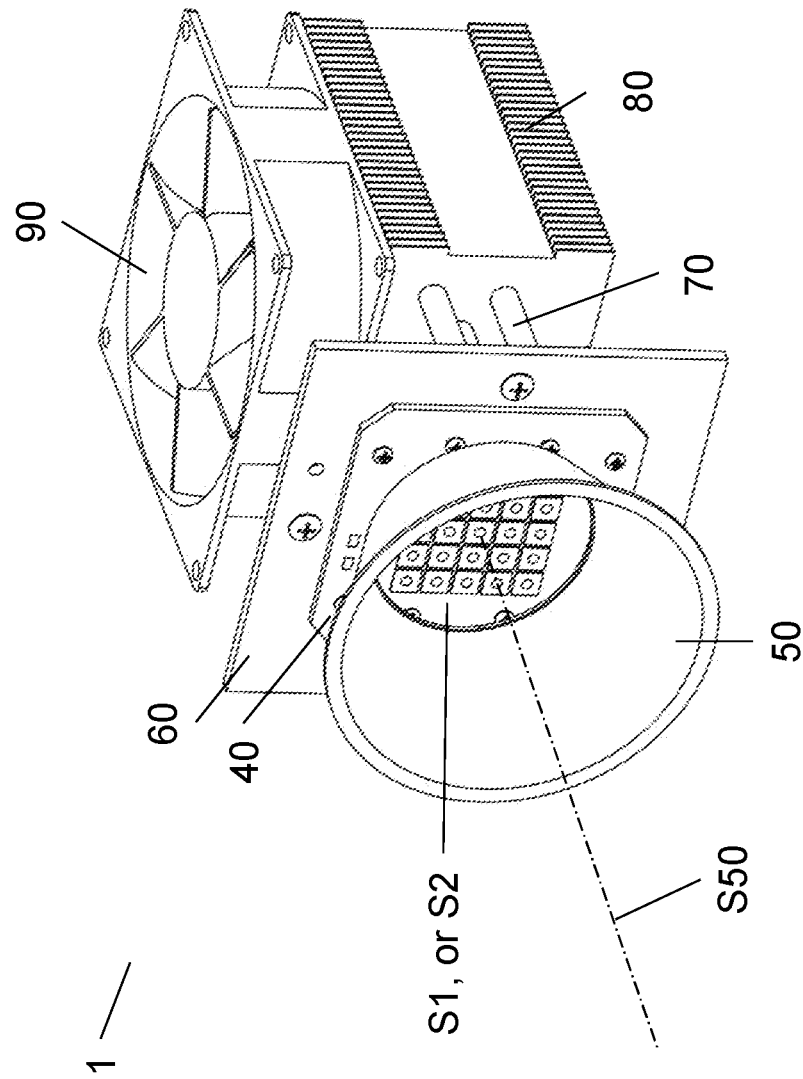
FIG. 1A shows a perspective view of a deep UV light source assembly according to an embodiment of this disclosure.
Figure 1B:
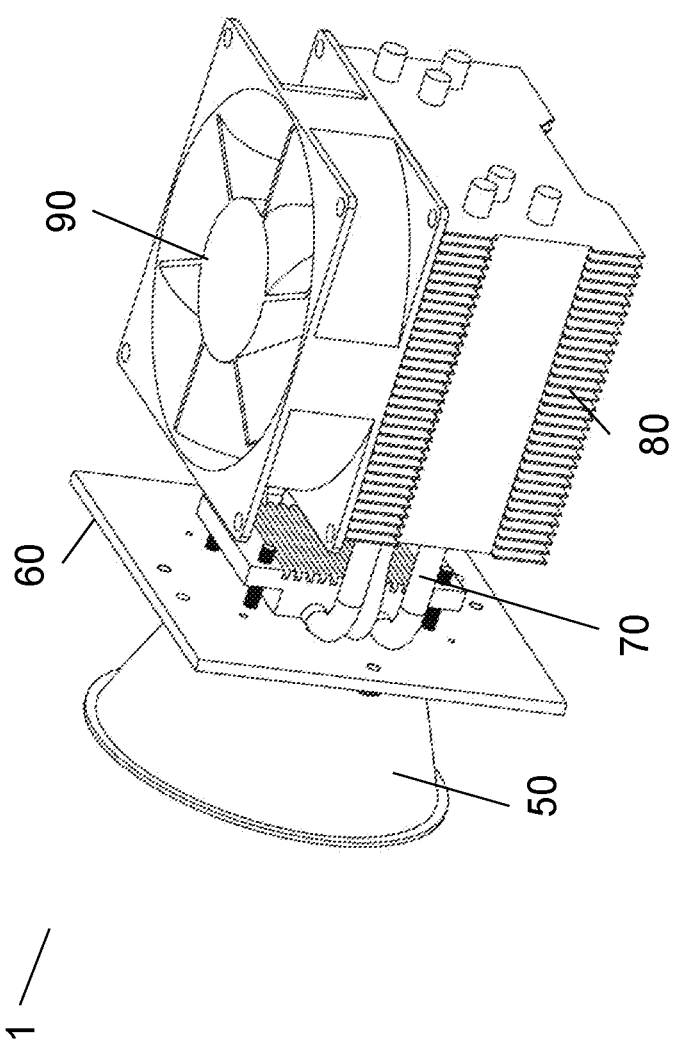
FIG. 1B shows a perspective view of a deep UV light source assembly according to an embodiment of this disclosure.
Figure 2A:
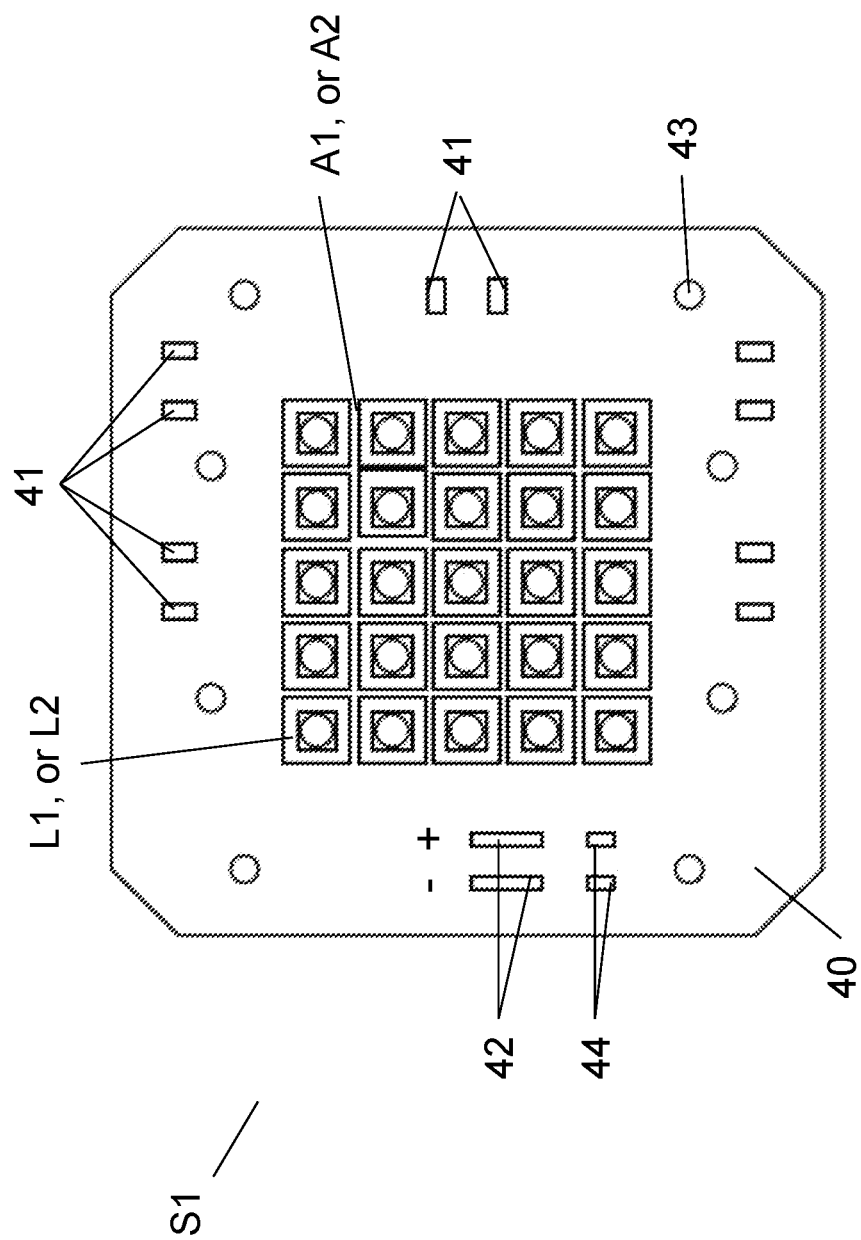
FIG. 2A presents a schematic plan view of a deep UV light source module according to an embodiment of this disclosure.

Two perspective views of a DUV light source assembly 1 according to an embodiment of this disclosure are shown in FIGS. 1A and 1B. The DUV light source assembly includes a DUV light source module S1 or S2, a reflector 50, a heat sink 60, a heat pipe 70, a radiator 80 and a fan 90. The schematic plan views of DUV light source module S1 and S2 are shown in FIGS. 2A and 5, respectively. As seen from FIG. 2A, DUV light source module S1 includes a print circuit board (PCB) 40, an array (A1 or A2) of DUV light-emitting diodes (LEDs), a plurality of LED drivers 41, a pair of electrical connectors 42, optionally a pair of solder pads 44, and a plurality of fastening holes 43. The DUV LED array A1 is made of multiple individual DUV LEDs (L1 or L2), whose structure will be discussed in detail in the following content. PCB 40 can be a metal core (such as copper) PCB (MCPCB) for good heat spreading and conduction. A possible equivalent electrical circuit of DUV light source module S1 is shown in FIG. 2B, where the DUV LEDs L1, or L2 are connected in an m×n matrix, i.e., n (columns) branches of LEDs connected in parallel, and each branch contains m (rows) LEDs connected in series. Each branch of LEDs has its own LED driver 41, which can be a constant current driver. Driver 41 can set up a constant operation current for the branch under its control. As shown, this configuration ensures that all LEDs are driven at the right operation current even if some LEDs start to degrade such as start to leak. In the embodiment shown in FIG. 2B, each branch of LEDs is connected to two parallel arranged drivers 41 at one end of the branch.

In another embodiment of DUV light source module S1, whose equivalent circuit is illustrated in FIG. 2C, LED array A1 may contain an array A11 of DUV LEDs L1 or L2, and an array A12 of LEDs L3 of a wavelength other than that of L1 and L2. For examples, LEDs L3 can be visible LEDs, intermixing with DUV LEDs L1 or L2 in the array A11 to manifest DUV light pattern emitted by the array A11. For example, LEDs L3 can be white LEDs for general illumination. Or, LEDs L3 can be near UV LEDs for contamination detection through near UV excited photoluminescence. In this embodiment, the arrays A11 of DUV LEDs L1 or L2 and A12 of LEDs L3 are driven by drivers 41 and 41', respectively. More specifically, the branches of DUV LEDs L1 or L2 and LEDs L3 are alternately arranged and driven by drivers 41 and 41', respectively. For example, FIG. 2C explicitly shows 3 branches of DUV LEDs L1 or L2 are alternately arranged with 3 branches of LEDs L3, with each branch containing 5 LEDs. The drivers 41 and 41' can share a common ground but be biased to different voltages. For example, the branches of DUV LEDs L1 or L2 with drivers 41 and the branches of LEDs L3 with drivers 41' can be biased to a different voltages V1 and V2, respectively. V1 can be larger than V2, for example, V1 can be in the range of 25-35V, V2 can be in the range of 15-17.5V, and V1 is larger than V2 by 10-17.5V.

Generally, the DUV LEDs L1, or L2 are connected in an m×n matrix, the LEDs L3 are connected in an m'×n' matrix, i.e., n (n') branches of LEDs connected in parallel, and each branch contains m (m') LEDs connected in series, where m may or may not equal to m', and n may or may not equal to n'. In some embodiments, m may be in the range of 2-20, m', may be in the range of 2-20, n may be in the range of 2-20, and n' may be in the range of 2-20.

Figure 2D:
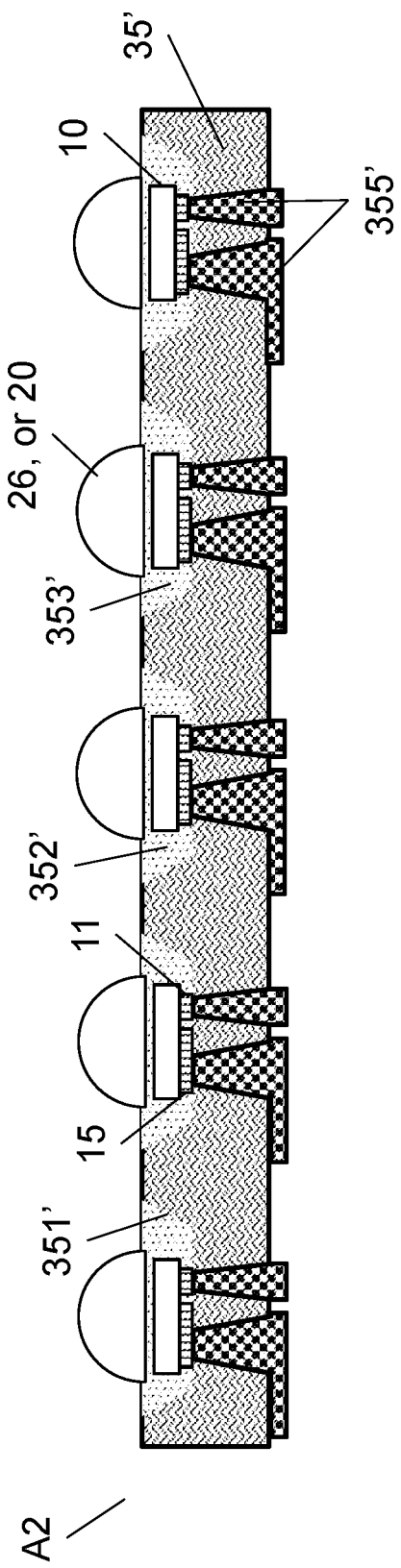
FIG. 2D presents a schematic cross-sectional view of a deep UV light-emitting diode array according to an embodiment of this disclosure.

In another embodiment, DUV light source module S1 includes a DUV LED array A2, and a schematic cross-sectional view of DUV LED array A2 is presented in FIG. 2D. As seen, DUV LED array A2 has an integrated silicon (Si) submount 35', which is electrical insulating and contains an array of cavities 352' with slanted reflective sidewall 351'. In an embodiment, integrated Si submount 35' is a pieces of high-resistivity plane (100) Si, and the slanted reflective sidewall is formed by plane (111) Si. When using etchant such as alkaline etchant KOH, NaOH, NH$_4$OH, et al to etch (100) Si, cavities can be formed as etch rate in crystal Si is anisotropic, plane (111) Si possessing the lowest etch rate (~400 times lower) than plane (110) and (100). As a result, cavities with a bottom of plane (100) Si and sidewalls of plane (111) Si can be formed. And the sidewalls are slanted to the bottom surface by an angle of 54.7° (which is the angle between Si (111) and (100) planes). Such sidewalls formed by crystal etch planes are very smooth and can be coated by DUV reflective materials such as aluminum (Al) to form DUV reflective sidewalls.

Integrated Si submount 35' also contains multiple pairs of through-silicon via (TSV) bond pads 355', which on one side bond to respective n- and p-bond pads (11, 15) of DUV LED chip 10 and on the other side bond to respective n- and p-bond pads on PCB 40. Cavities 352' can be filled with cavity filler 353', which can be DUV transparent epoxy material such as fluoropolymer with refractive index larger than 1.2, or larger than 1.3. Further, cavity filler 353' can be used to attach lens 26 or nested lens 20 (will be detailed in the following content) to DUV LED chip 10.

Referring to FIGS. 1A and 1B, DUV light source module S1 is fastened to heat sink 60, which is made of high-thermal-conductivity materials such as gold (Au), diamond, copper (Cu), aluminum (Al), and the like. A part of heat pipes 70 is then attached to heat sink 60, and radiator 80 is fastened to and contacted with another part of heat pipes 70. Fan 90 can blow air through radiator 80. During operation, heat generated by DUV light source module S1 will be transferred to heat sink 60 and then conducted to the part of heat pipes 70 which is attached to heat sink 60, making the phase-changing media within heat pipes 70 vaporize and carrier heat to the other part of heat pipes 70 which is fastened to radiator 80 and cooled by fan 90. Vaporized phase-changing media is cooled and condensed by radiator 80 and fan 90, and flow back to the hotter ends of heat pipes (which is the part attached to heat sink 60) by siphon action or capillary effect. The above heat transfer process will keep going on and the temperature of PCB 40 of DUV light source module S1 will be kept at relatively low temperature, such as less than 40° C., or less than 38° C.

Also attached to, or disposed at the vicinity of, DUV light source module S1 is a reflector 50, which can be a cone-shaped reflector or a paraboloidal/parabolic-shaped reflector for confining and reshaping the light beam emitted by DUV light source module S1. Reflector 50 may have a suitable aperture to focus and reshape the light beam. In this specification, the term aperture refers to the opening through which all light rays leave the reflector. The reflecting surface of reflector 50 can be specular such as coated with aluminum film or electroplated with aluminum film, or diffusive such as coated with micro teflon (polytetrafluoroethylene (PTFE)). The reflectance of reflector 50 is optionally to be no less than 80%, or no less than 90%. LED array A1 or A2 of DUV light source module S1 and reflector 50 are preferably to be symmetrical and co-axial, where the co-axis is called the optical axis S50. Light beam delivered by DUV light source module S1 and confined and reshaped by reflector 50 is preferred to be symmetrical about the optical axis S50.

Figure 3:
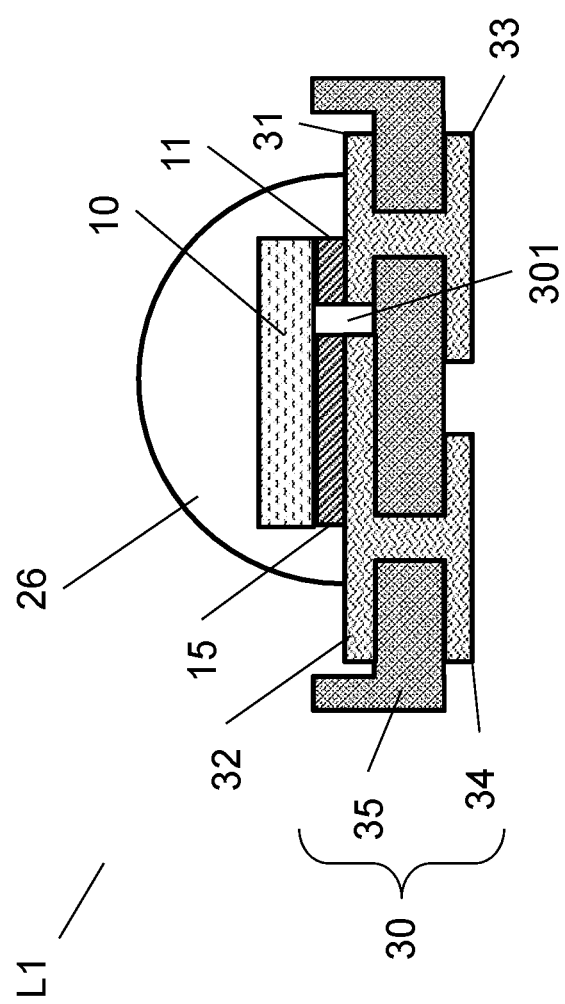
FIG. 3 illustrates a schematic cross-sectional view of a surface mount deep UV light-emitting diode according to an embodiment of this disclosure.

LEDs L1 used to make LED array A1 are surface mount device (SMD) DUV LEDs, with a possible cross-sectional illustration shown in FIG. 3. As seen, LED L1 includes three major parts: DUV LED chip 10, surface mount (SM) 30, and lens 26. SM 30 includes an electrically insulating body (SM body) 35, and four bond pads 31-34, where bond pads 31 and 32 are to receive bond pads 11 (n-bond pad), and 15 (p-bond pad) of chip 10, respectively, and bond pads 33 and 34 are to be bonded to respective n- and p-bond pads on PCB 40. Bond pads 31 and 33, 32 and 34 are electrically connected via metal through vias, respectively. Bond pad 15 being p-bond pad of LED chip 10 is much larger than bond pad 11 which is n-bond pad of chip 10. According to the present disclosure, the area of p-bond pad 15 is at least 60% of the area of LED chip 10, for example, being 65%-78% of the chip area, whereas the area of n-bond pad 11 is about 10%-45% of the chip area. This arrangement can reduce thermal resistance from LED chip 11 to surface mount 30, for example, ensuring the thermal resistance from the PN junction of chip 11 to surface mount 30 to be less than 4° C./W, preferably less than 3° C./W. Isolation 301 is formed between bond pads 11 and 15, and between bond pads 31 and 32 for electrical isolation. It can be an airgap, or an insulation fill such as epoxy fill.

Lens 26 is formed on LED chip 10. Optionally part of lens 26 can also be formed on SM 30. Lens 26 with shape being part of a sphere or a hemisphere can be made of DUV transparent materials with refractive index in between 1.3 to 2.4, such as certain fluoropolymer, quartz, sapphire, AlN, et al. When lens 26 being hemispheric, LED L1 usually delivers a wide-angle light cone, with a cone angle at half intensity more than 100 degree, for example, being 150 degree.

Figure 4:
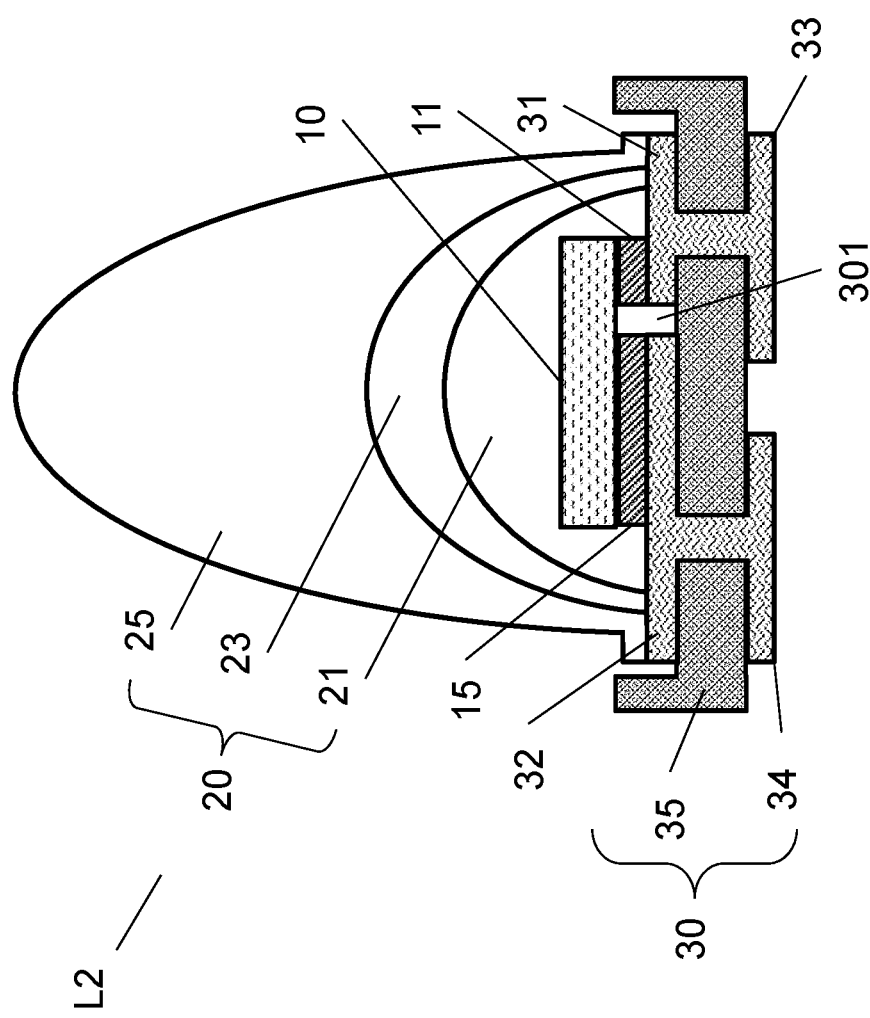
FIG. 4 illustrates a schematic cross-sectional view of a surface mount deep UV light-emitting diode according to an embodiment of this disclosure.

Another type of LED, LED L2 used to make LED array A1 is similar to LED L1, with the difference that LED L2 has a nested lens 20. The cross-sectional illustration of LED L2 is shown in FIG. 4. As seen, nested lens 20 includes three parts, a spheric or hemispheric (HS) lens 21, an inter-lens cavity 23, and a tall lens 25 (taller than lens 21). The inter-lens cavity 23 physically separates lens 21 and tall lens 25. The inter-lens cavity 23 is DUV light transparent and has a lower refractive index than those of lenses 21 and 25. Optionally, inter-lens cavity 23 is an air gap. Inter-lens cavity 23 can also be filled with proper transparent filling material. Tall lens 25 may have refractive index equal to or larger than that of lens 21. Tall lens 25 can be an aspheric lens (AS), it can be part of a prolate spheroid. In an embodiment, lens 21 is a hemisphere lens of a radius about 1250 µm, tall lens 25 is hemi prolate spheroid with semi-diameters about 1600, 1600 and 3000 µm, where lens 21 sits in the inter-lens cavity 23 and the narrowest distance between lens 21 and tall lens 25 is about 50 µm. Nested lens 20 can narrow the light beam as compared to hemisphere lens 26 or 21. For example, LED L2 adopting nested lens 20 can deliver a narrow-angle light cone, with a cone angle at half intensity less than 40 degree, for example, being 35 degree. Nested lens 20 also extracts more light out of LED chip 10 as compared to a single tall lens 25.

DUV light source module S2, whose schematic plan view is shown in FIG. 5, can also be used as light source for the DUV light source assembly shown in FIGS. 1A and 1B. It mainly differs from DUV light source module S1 in terms of the LED chip packaging technology. For DUV light source module S1, LED chips 10 are firstly flip-chip mounted to surface mount 30 or integrated silicon submount 35' before being placed onto PCB 40. In DUV light source module S2, LED chips 10 are directly bonded to PCB 40, optionally with subsequently formed lens 26 or nested lens 20 on chips 10 to form an array of chip-on-board (COB) LEDs 10' (COB array A2'). With the omission of surface mount 30, DUV light source module S2 may have better thermal performance. DUV light source module S2 may also have a transient voltage suppression (TVS) or Zener diode 45 to provide electrostatic discharge (ESD) protection of COB array A2'. TVS diode 45 is in parallel connection to COB array A2', in order to suppress/filter harmful voltage surges to COB array A2'. Suppose COB array A2' is made of m×n DUV LEDs, i.e., n (columns) branches of LEDs connected in parallel, and each branch contains m (rows) LEDs connected in series, and suppose in a branch a $i^{th}$ LED can survive a maximal forward voltage $V_{Fi}$ and a maximal reverse voltage $V_{Ri}$, therefore the selection of TVS diode 45 requires that the forward and reverse turn-on voltages of TVS diode 45 to be equal or close to $\Sigma_{i=1}^{m} V_{Fi}$ and $\Sigma_{i=1}^{m} V_{Ri}$, respectively. Upon turn-on (forward or reverse), TVS diode 45 is of negligible resistance therefore bypasses all voltage surge related current to protect COB array A2'. For example, suppose COB array A2' is made of 5×5 DUV LEDs, and the maximal forward and maximal reverse voltages of each LED are 7.5V and −5V, respectively. Therefore, TVS diode 45 to protect this 5×5 DUV LED COB array A2' needs to have forward and reverse turn-on voltages of about 37.5 and −25 V, respectively.

Figure 6A:
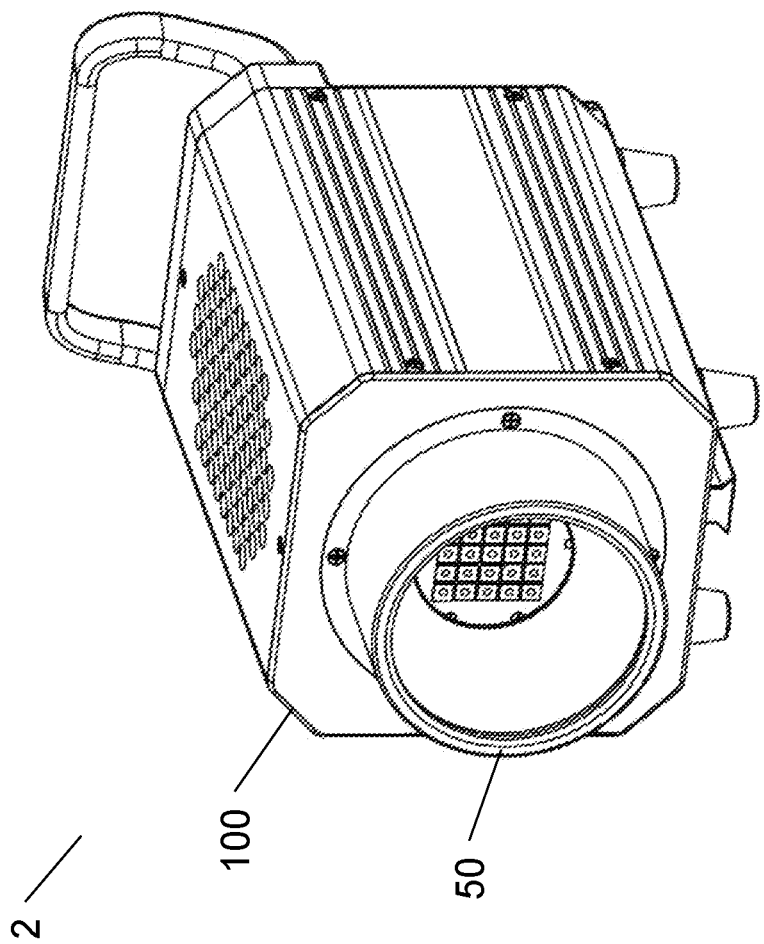
FIG. 6A presents a perspective view of a deep UV light source apparatus according to an embodiment of this disclosure.
Figure 6B:
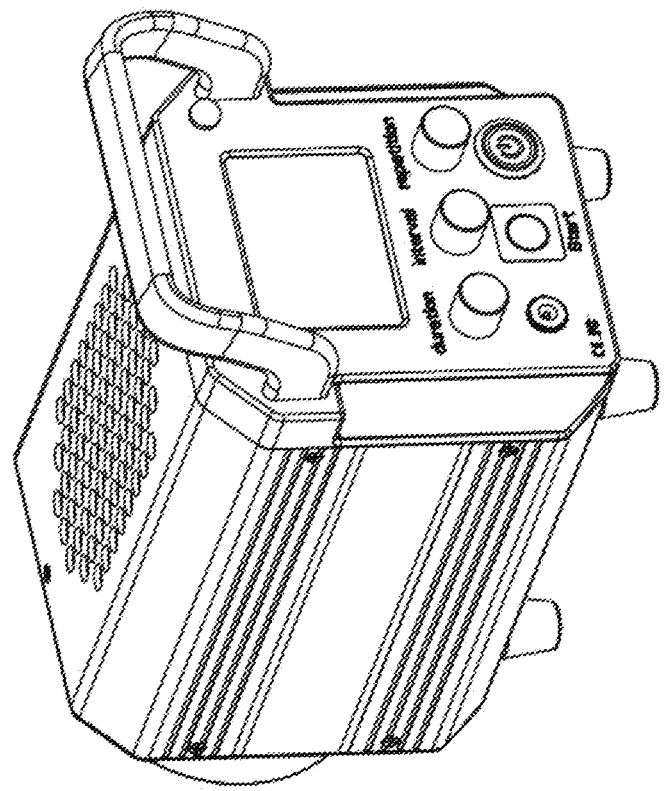
FIG. 6B presents a perspective view of a deep UV light source apparatus according to an embodiment of this disclosure.

DUV light source assembly 1 shown in FIGS. 1A and 1B with aid of some function electronics and mechanical enclosure (100) can be assembled and packaged into DUV light source apparatus 2 as shown in FIGS. 6A and 6B. The function electronics used in DUV light source apparatus 2 may include, but not limited to, operator inputs, microprocessor, human sensor, distance sensor and status display. According to one aspect of the present disclosure, reflector 50 can be fastened onto enclosure 100 to be at the vicinity of the DUV light source module (S1 or S2). The fastening methods such as using screws or threads allow for easy swap of reflectors to obtain different sizes of disinfection light beams for different areas of disinfection. For example, for large area disinfection, a reflector of a large aperture may be used. When disinfecting small areas, a reflector of a small aperture may be used so that light beam is more focused in a smaller area.

Figure 6C:
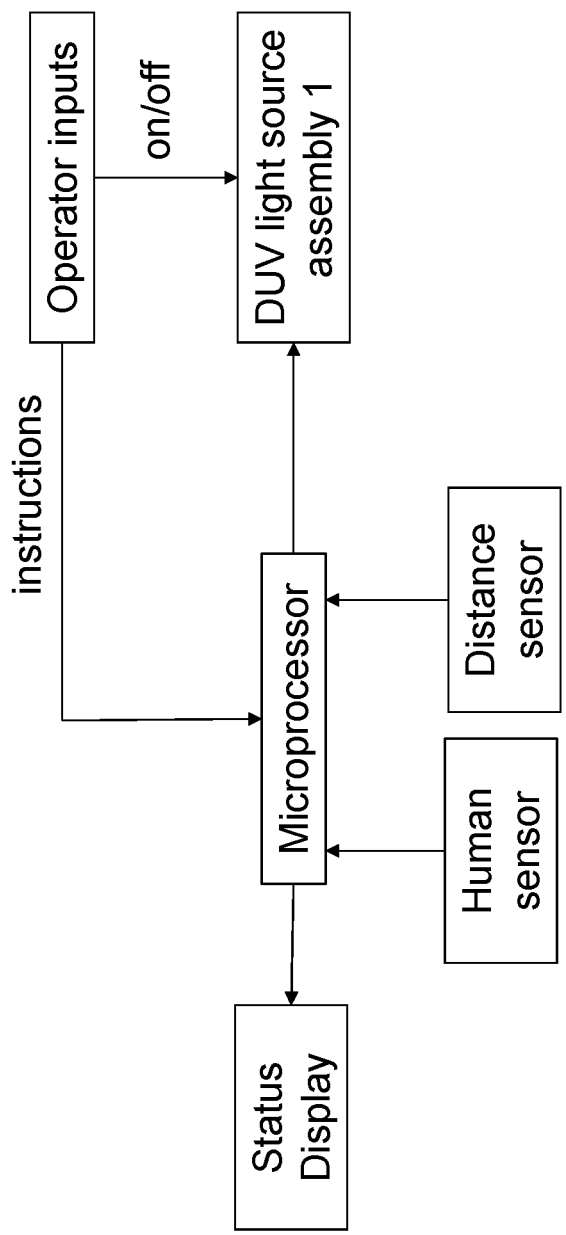
FIG. 6C presents a control logic diagram of a deep UV light source apparatus according to an embodiment of this disclosure.

A control logic diagram for a deep UV light source apparatus according to this disclosure is presented in FIG. 6C, which includes operator inputs, microprocessor, human sensor, distance sensor and status display. As seen, Operator has the highest priority, can directly turn on/off DUV light source assembly 1, can also deliver instructions/programs to Microprocessor to turn on/off assembly 1 with desired sequence. The DUV light source apparatus 2 taking orders from Operator and/or Microprocess can deliver DUV light in a continuous mode (turn on assembly 1 for a continuous period of time), or a pulse mode (turn DUV light on and off alternately for many cycles). The human sensor is to detect the presence of human in its proximity, especially to detect the existence of human in line of sight of its DUV light cone delivered by DUV light source assembly 1. If there is human in light of sight of the DUV light cone, the human sensor will send a positive signal to Microprocess to turn off the DUV light. The human sensor can be a combination of motion sensor and infrared sensor. The distance sensor is to detect the distance between DUV light source assembly 1 (i.e., the surface of the DUV light source) and the surface intended to be disinfected. It can be radar, lidar, infrared, or ultrasonic distance sensor. When Microprocess receives the distance from DUV light source assembly 1 to the surface of disinfection, it can use its DUV intensity database to determine a disinfection time for a predetermined disinfection dose requirement. The status display is to display the history and the ongoing disinfection progress, displaying the historically accumulated disinfection time and current ongoing disinfection time, dosage, and percentage to completion of the ongoing disinfection.

A DUV intensity database is stored in Microprocessor, containing spatial DUV intensity data, which are measured after manufacture. DUV intensity depends on the output power of DUV light source module S1 or S2, lens structure (such as single lens or nested lens) used for the DUV LEDs, and reflector 50.

Figure 7A:
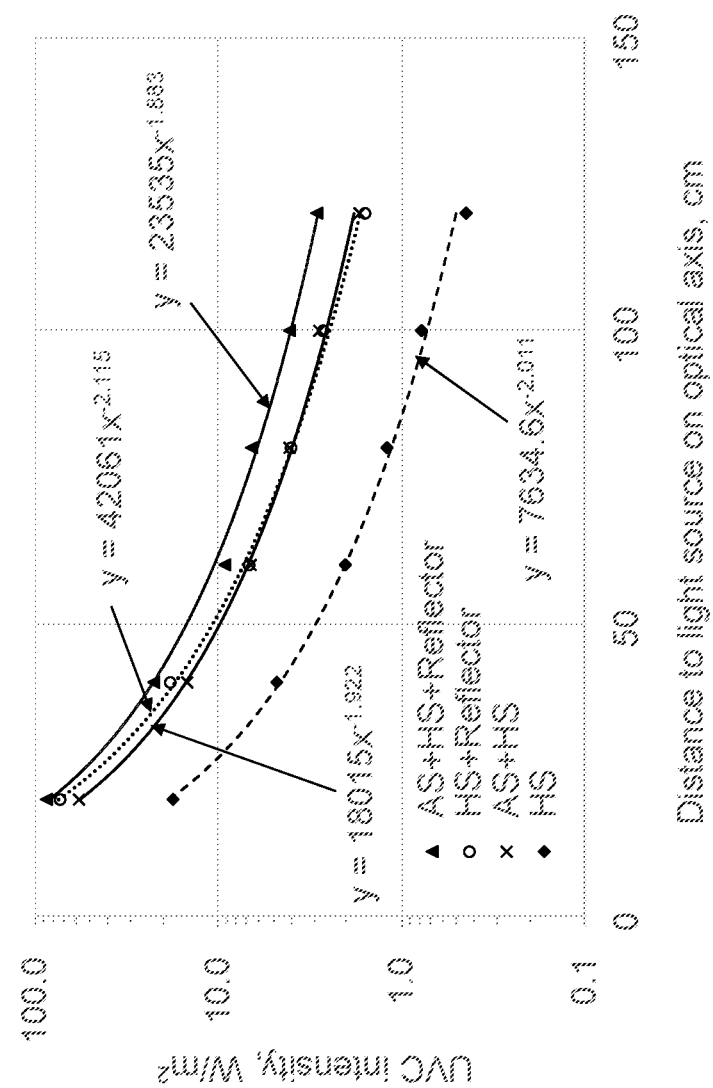
FIG. 7A plots UVC intensity profiles along optical axis for different deep UV light source apparatuses according to an embodiment of the present disclosure.
Figure 7B:
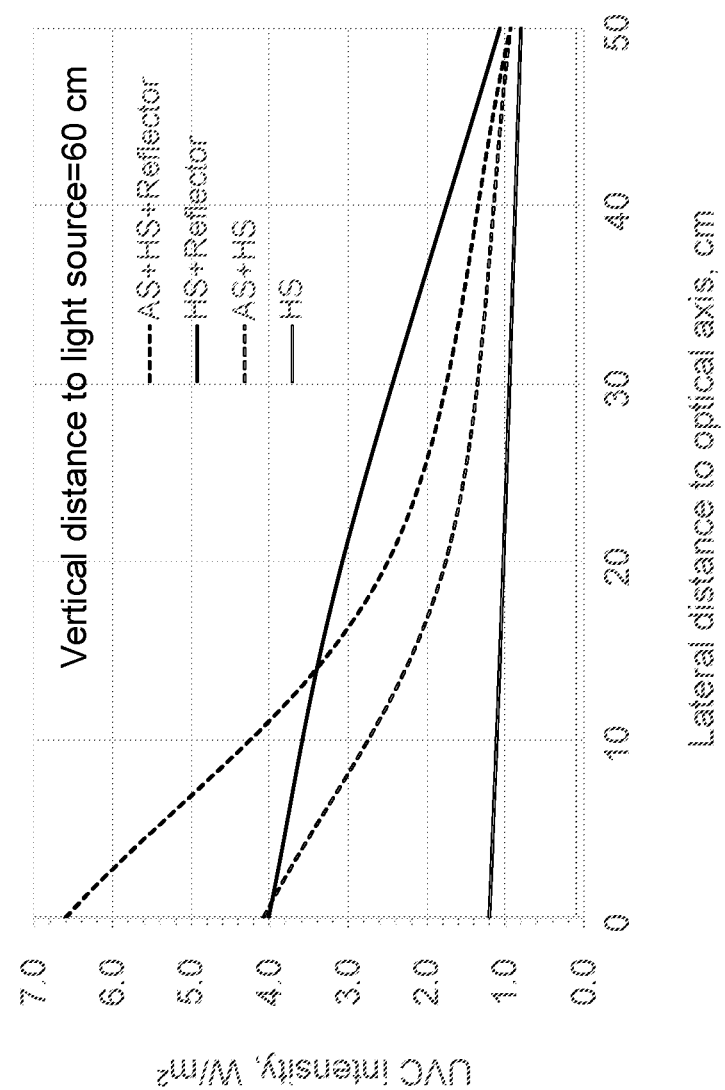
FIG. 7B plots lateral UVC intensity profiles at z=60 cm on optical axis for different deep UV light source apparatuses according to an embodiment of the present disclosure.

As examples, some DUV light source apparatuses are made with DUV light source modules S1, having 5×5 LEDs L1 or L2, with or without a reflector. Portions of DUV intensity data of these apparatuses were measured and plotted along optical axis (S50) in FIG. 7A, and, in a direction perpendicular to optical axis (S50) at distance 60 cm away from DUV light source module S1 in FIG. 7B, respectively.

As seen, all the DUV intensity data along optical axis can be fitted well with equation $I=I_0 x^{-(2\pm\delta)}$ and $\delta$ is a small number ($\delta \leq 0.12$), indicating the intensity on optical axis is roughly inversely proportional to the distance to DUV light source module. Legends HS and AS+HS mean that the LEDs were capped with hemisphere (HS) lenses and nested lenses, respectively. With LEDs capped by lenses and DUV light source modules equipped with reflectors, these DUV light source apparatus can maintain DUV intensity larger than 2.0 W/m² (0.2 mW/cm²) on the optical axis at or more than 1 meter away from the DUV light source modules. This means that within 50 seconds a dosage of more than 10 mJ/cm2 will be delivered, which is large enough to disinfect most microbes with reduction rate more than 99.9%. Also, nested lenses improve DUV intensity but enlarge intensity lateral nonuniformity, as compared to HS lenses. Reflector (50) further enhances DUV intensity within the light cone.

According to another aspect of this disclosure, to improve the DUV intensity and uniformity of DUV light source apparatuses, the DUV LEDs at or close to the center of the array A1 (preferably, optical axis S50 meets the center) therefore can be capped with HS lenses (becoming LEDs L1) and the DUV LEDs at or close to the perimeter of the array A1 can be capped with nested lenses (becoming LEDs L2). For example, for array A1 of 5×5 DUV LEDs, the 16 LEDs on the perimeter can be L2 type LEDs and the 9 (3×3) LEDs at the center part can be L1 type LEDs; For array A1 of 6×6 DUV LEDs, the 20 LEDs on the perimeter can be L2 type LEDs and the 16 (4×4) LEDs at the center part can be L1 type LEDs; For array A1 of 7×7 DUV LEDs, the 24 LEDs on the perimeter can be L2 type LEDs and the 25 (5×5) LEDs at the center part can be L1 type LEDs; For array A1 of 10×10 DUV LEDs, the 64 LEDs on the perimeter can be L2 type LEDs and the center 36 (633 6) LEDs can be L1 type LEDs; et cetera. Or, for array A1 of 10×10 DUV LEDs, the 36 LEDs on the perimeter can be L2 type LEDs and the center 64 (8×8) LEDs can be L1 type LEDs.

Figure 8:
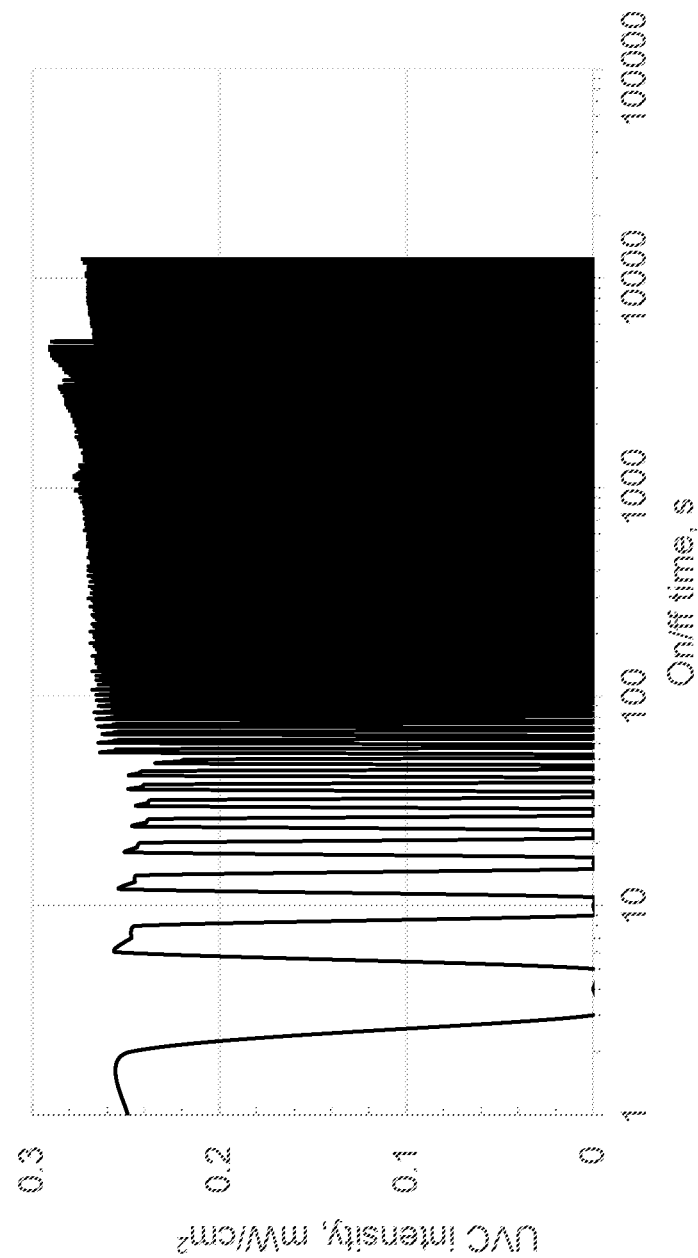
FIG. 8 plots the short pulse on/off characteristics of a 5×5 SMD6060 UVC LED light source apparatuses according to an embodiment of the present disclosure.

DUV light source apparatus made according to the present disclosure can be turned on/off instantly. That means, it can be operated in a pulse mode to improve device lifetime. The pulse operation characteristic of a DUV light source apparatus is shown in FIG. 8, wherein the microprocess rapidly turned DUV light source module (S1) on and off each for 3 seconds for about 1500 times, and a DUV photodetector was placed 1 meter away from the DUV light source module along the optical axis and the DUV light intensity was recorded. As seen, the DUV light source apparatus can be rapidly turned on and off, and the high frequency on/off operations result in no degradation of DUV light intensity, maintaining ~2.4 W/m², or 0.24 mW/cm² before and after the whole pulse operations.

Figure 9:
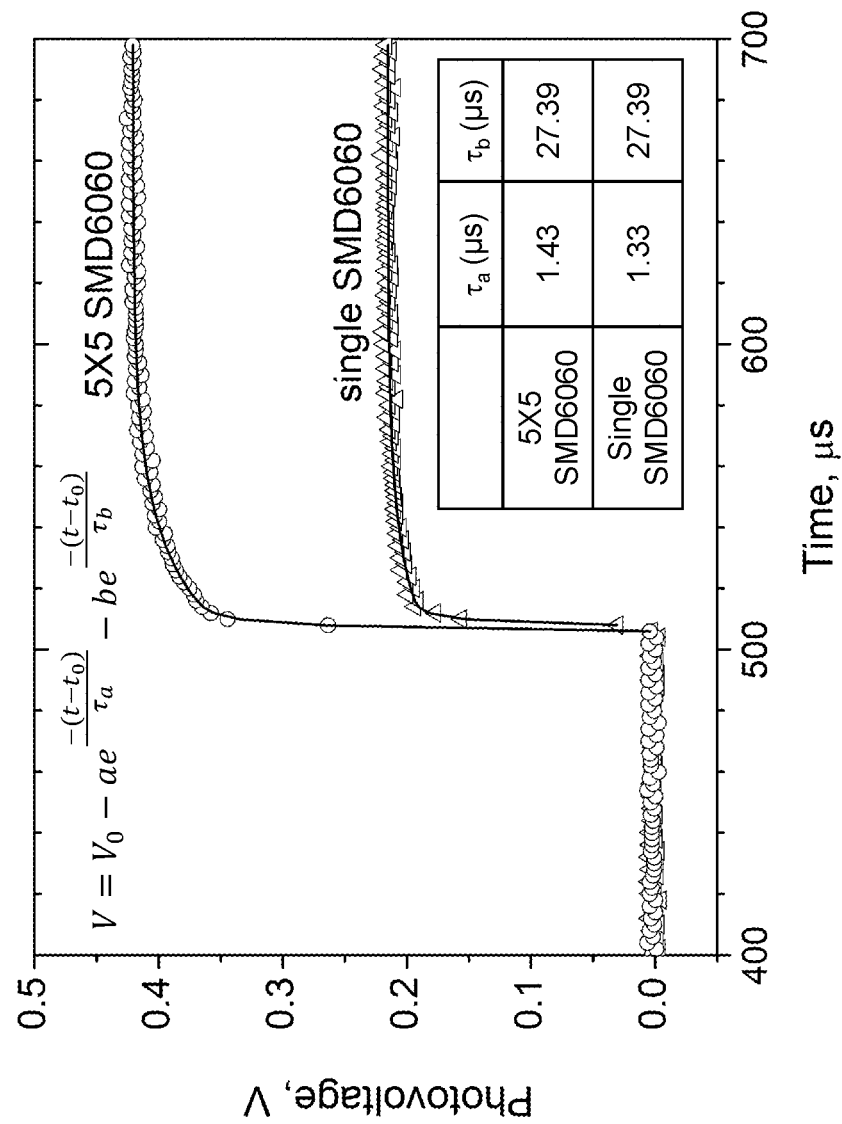
FIG. 9 compares the turn-on transient processes of a SMD6060 UVC LED and a 5×5 SMD6060 UVC LED light source apparatuses according to an embodiment of the present disclosure.

To investigate more accurately on the instant-on characteristic, a high-precision pulse current source was used to drive a single DUV LED L1 and a DUV light source apparatus with an array A1 of 5×5 DUV LEDs L1, with a current pulse resolution of about 2 µs. The turn on of the DUV LED and DUV light source apparatus was again monitored by a DUV photodetector which was in parallel connection to a resistor (560 Ω) so as to facilitate a current source to measure the photovoltage generated by the photodetector upon receiving DUV photons. The measurement data (open triangles and circles) and simulation data (solid lines) are shown in FIG. 9. As seen, the photovoltage response is very fast and can be simulated by a function, $$V = V_0 - ae^{\frac{-(t-t_0)}{\tau_a}} - be^{\frac{-(t-t_0)}{\tau_b}}.$$

The two transient time constants, $\tau_a$ and $\tau_b$, are related to two equivalent resistor-capacitor (RC) circuits, one from the DUV LED (or DUV light source apparatus) and the other from the photodetector connected in parallel to the 560 Ω resistor. As seen, the transient time constants for the DUV LED and the DUV light source apparatus are very similar, with $\tau_a=1.33$ or 1.43 µs and $\tau_b=27.39$ µs. As the photodetector is connected to a large resistor (560 Ω), it is believed that slower transient time constant $\tau_b$ is due to the photodetector-resistor RC circuit. This means that the DUV LED and DUV light source apparatus with 5×5 DUV LEDs has very fast turn-on properties, with characteristic transient time less than of 2 µs, which is about the current measurement resolution.

The present invention has been described using exemplary embodiments. However, it is to be understood that the scope of the present invention is not limited to the disclosed embodiments. On the contrary, it is intended to cover various modifications and similar arrangement or equivalents which can be obtained by a person skilled in the art without creative work or undue experimentation. The scope of the claims, therefore, should be accorded the broadest interpretation so as to encompass all such modifications and similar arrangements and equivalents.

What is claimed is:

1. A DUV light source module comprising a print circuit board, an array of DUV light-emitting diodes (LEDs), a plurality of DUV LED drivers for driving the DUV light-emitting diodes, and a pair of electrical connectors for connecting the DUV LED drivers, hence the DUV light-emitting diodes, to a power source, wherein the array of DUV light-emitting diodes comprises an integrated silicon (Si) submount and a plurality of LED chips, the integrated silicon submount is electrical insulating and contains an array of cavities with slanted reflective sidewall; each of the LED chips is disposed in a corresponding cavity of the array of cavities, respectively; and the integrated silicon submount is bonded on the print circuit board, wherein the DUV light-emitting diodes are connected in an m×n matrix, including n branches of LEDs connected in parallel, each branch of LEDs contains m DUV LEDs connected in series and has its own DUV LED driver.

2. The DUV light source module of claim 1, wherein the integrated silicon submount is a piece of plane (100) Si, and the slanted reflective sidewall of the cavities is formed by plane (111) Si and a bottom of the cavities is formed by plane (100) Si.

3. The DUV light source module of claim 1, wherein the slanted reflective sidewall is coated with a DUV reflective material.

4. The DUV light source module of claim 1, wherein each of the cavities contains a pair of through-silicon via (TSV) bond pads, one side of the through-silicon via (TSV) bond pads bonds to respective n- and p-bond pads of a corresponding LED chip, and the other side of the through-silicon via (TSV) bond pads bonds to respective n- and p-bond pads on the print circuit board.

5. The DUV light source module of claim 1, wherein the cavities are filled with a DUV transparent filler with a refractive index larger than 1.2.

6. The DUV light source module of claim 1, wherein a nested lens is formed on each of the LED chips, the nested lens includes a spheric or hemispheric lens, an inter-lens cavity, and a tall lens taller than the spheric or hemispheric lens, the inter-lens cavity physically separates the spheric or hemispheric lens and the tall lens, being DUV light transparent and having a refractive index lower than that of the spheric or hemispheric lens and the tall lens.

7. The DUV light source module of claim 6, wherein the inter-lens cavity is an air gap, or filled with DUV transparent material.

8. The DUV light source module of claim 6, wherein the tall lens has a refractive index equal to or larger than that of spheric or hemispheric lens.

9. The DUV light source module of claim 1, further comprising an array of visible light-emitting diodes and a plurality of visible LED drivers, wherein the visible light-emitting diodes are connected in an m'xn' matrix, including n' branches of LEDs connected in parallel, each branch of LEDs contains m' visible LEDs connected in series and has its own visible LED driver, and the n branches of DUV LEDs and the n' branches of visible LEDs are arranged alternately.

10. The DUV light source module of claim 1, further comprising an electrostatic discharge (ESD) or transient voltage suppression (TVS) protector disposed on the print circuit board.

11. A DUV light source device comprising a DUV light source module, a reflector, a heat sink, a heat pipe, a radiator and a fan,
the DUV light source module comprising a print circuit board, an array of DUV light-emitting diodes (LEDs), a plurality of DUV LED drivers for driving the DUV light-emitting diodes, and a pair of electrical connectors for connecting the DUV LED drivers, hence the DUV light-emitting diodes, to a power source,
wherein the array of DUV light-emitting diodes comprises an integrated silicon (Si) submount and a plurality of LED chips, the integrated silicon submount is electrical insulating and contains an array of cavities with slanted reflective sidewall; each of the LED chips is disposed in a corresponding cavity of the array of cavities, respectively; and the integrated silicon submount is bonded on the print circuit board,
wherein the DUV light source module is fastened to the heat sink, a part of the heat pipe is attached to the heat sink, and the radiator is fastened to and in contact with another part of the heat pipe, the fan blow air through the radiator; during operation, heat generated by the DUV light source module is transferred to the heat sink and then conducted to the part of the heat pipe attached to the heat sink, making a phase-changing media within the heat pipe vaporize and carrier heat to the another part of the heat pipe which is fastened to the radiator and cooled by the fan.

12. A DUV light source module comprising a print circuit board, an array of DUV light-emitting diodes (LEDs), a plurality of DUV LED drivers for driving the DUV light-emitting diodes, and a pair of electrical connectors for connecting the DUV LED drivers, hence the DUV light-emitting diodes, to a power source,
wherein the array of DUV light-emitting diodes comprises an integrated silicon (Si) submount and a plurality of LED chips, the integrated silicon submount is electrical insulating and contains an array of cavities with slanted reflective sidewall; each of the LED chips is disposed in a corresponding cavity of the array of cavities, respectively; and the integrated silicon submount is bonded on the print circuit board,
wherein a nested lens is formed on each of the LED chips, the nested lens includes a spheric or hemispheric lens, an inter-lens cavity, and a tall lens taller than the spheric or hemispheric lens, the inter-lens cavity physically separates the spheric or hemispheric lens and the tall lens, being DUV light transparent and having a refractive index lower than that of the spheric or hemispheric lens and the tall lens.

13. The DUV light source module of claim 12, wherein the inter-lens cavity is an air gap, or filled with DUV transparent material.

14. The DUV light source module of claim 12, wherein the tall lens has a refractive index equal to or larger than that of spheric or hemispheric lens.

15. The DUV light source module of claim 12, wherein the integrated silicon submount is a piece of plane (100) Si, and the slanted reflective sidewall of the cavities is formed by plane (111) Si and a bottom of the cavities is formed by plane (100) Si.

16. The DUV light source module of claim 12, wherein the slanted reflective sidewall is coated with a DUV reflective material.

17. The DUV light source module of claim 12, wherein each of the cavities contains a pair of through-silicon via (TSV) bond pads, one side of the through-silicon via (TSV) bond pads bonds to respective n- and p-bond pads of a corresponding LED chip, and the other side of the through-silicon via (TSV) bond pads bonds to respective n- and p-bond pads on the print circuit board.

18. The DUV light source module of claim 12, wherein the cavities are filled with a DUV transparent filler with a refractive index larger than 1.2.

* * * * *